United States Patent
Hoctor et al.

(10) Patent No.: US 7,621,876 B2
(45) Date of Patent: Nov. 24, 2009

(54) CONTINUOUS, NON-INVASIVE TECHNIQUE FOR DETERMINING BLOOD PRESSURE USING A TRANSMISSION LINE MODEL AND TRANSCUTANEOUS ULTRASOUND MEASUREMENTS

(75) Inventors: Ralph T. Hoctor, Saratoga Springs, NY (US); Lawrence T. Hersh, Tampa, FL (US); Bruce A. Friedman, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 1010 days.

(21) Appl. No.: 11/083,259

(22) Filed: Mar. 17, 2005

(65) Prior Publication Data

US 2006/0211942 A1 Sep. 21, 2006

(51) Int. Cl.
- A61B 5/02 (2006.01)
- A61B 5/103 (2006.01)
- A61B 5/117 (2006.01)
- A61B 8/00 (2006.01)
- A61B 8/14 (2006.01)

(52) U.S. Cl. .................. 600/504; 600/485; 600/483; 600/481; 600/587; 600/437; 600/438; 600/454; 600/465

(58) Field of Classification Search .............. 600/437, 600/438, 453–457, 466–468, 465, 481, 483, 600/485, 486, 488, 500–507

See application file for complete search history.

(56) References Cited

U.S. PATENT DOCUMENTS

| | | | |
|---|---|---|---|
| 5,857,975 A | | 1/1999 | Golub |
| 6,117,087 A * | | 9/2000 | Kamm et al. ............... 600/504 |
| 6,261,233 B1 * | | 7/2001 | Kantorovich ............... 600/454 |
| 6,264,611 B1 * | | 7/2001 | Ishikawa et al. ............ 600/486 |
| 6,647,287 B1 * | | 11/2003 | Peel et al. .................. 600/513 |
| 6,648,828 B2 | | 11/2003 | Friedman et al. |
| 6,676,600 B1 * | | 1/2004 | Conero et al. .............. 600/438 |
| 6,730,038 B2 | | 5/2004 | Gallant et al. |
| 7,125,383 B2 * | | 10/2006 | Hoctor et al. .............. 600/438 |
| 7,425,199 B2 * | | 9/2008 | Hoctor et al. .............. 600/485 |
| 2005/0015009 A1 * | | 1/2005 | Mourad et al. ............. 600/438 |
| 2005/0143640 A1 * | | 6/2005 | Hoctor et al. .............. 600/407 |

(Continued)

OTHER PUBLICATIONS

Cuff-Less Ambulatory Monitoring of Beat-to-Beat Blood Pressure Based on a Hemodynamic Model; Yi Zhang, Boo-Ho Yang, Haruhiko H. Asada, d'Arbeloff Laboratory for Information Systems and Technology; 1999 IEEE; p. 1029; Proceedings of The First Joint BMES/EMBS Conference Serving Humanity, Advancing Technology Oct. 13-16, '99 Atlanta, GA.

Primary Examiner—Charles A Marmor, II
Assistant Examiner—Navin Natnithithadha
(74) Attorney, Agent, or Firm—Andrus, Sceales, Starke & Sawall, LLP (57) ABSTRACT

A method and technique for the continuous, non-invasive measurement of blood pressure. The blood pressure measurement technique of the present invention utilizes ultrasound measurements to determine the diameter of the blood vessel in which the blood pressure is being measured as well as the flow rate of blood at both an input point and an output point along the blood vessel. The system utilizes a transmission line model to relate various blood vessel measurements with electrical components. The transmission line model, in combination with data management techniques including state variable representations and Kalman filtering, is used to develop a blood pressure measurement in real time.

19 Claims, 6 Drawing Sheets

U.S. PATENT DOCUMENTS

2005/0154299 A1* 7/2005 Hoctor et al. ............... 600/437
2006/0079773 A1* 4/2006 Mourad et al. .............. 600/438
2006/0211942 A1* 9/2006 Hoctor et al. ............... 600/438
2006/0241459 A1 10/2006 Tai

* cited by examiner

CONTINUOUS, NON-INVASIVE TECHNIQUE FOR DETERMINING BLOOD PRESSURE USING A TRANSMISSION LINE MODEL AND TRANSCUTANEOUS ULTRASOUND MEASUREMENTS

BACKGROUND OF THE INVENTION

The invention generally relates to an apparatus and method for measuring blood pressure, and more particularly to a continuous non-invasive blood pressure measurement and monitoring method and apparatus.

In the case of a hospitalized patient, it has long been desired to be able to provide non-invasive beat-by-beat (continuous) systolic and diastolic blood pressure values. Unfortunately, a practical and reliable solution for obtaining this type of information has yet to be developed.

One technique for providing a continuously measured blood pressure is to insert a saline filled catheter through the patient's vascular system to the point at which the blood pressure measurements are desired. The catheter is connected to a pressure sensor, which measures the pressure in the vessel. As an alternative method, a catheter with the pressure sensor at the tip that directly senses the blood pressure can be inserted into the patient's vascular system. Although both of these techniques have proven effective and continuously monitor a patient's blood pressure, both techniques involve making an incision into the patient's skin and inserting the catheter into the blood vessel. As a consequence, this invasive procedure entails some risk of complication to the patient and is in most cases undesirable.

As yet another alternative, procedures have been developed that favor a tonometric method that does require a blood pressure cuff. However, these methods still require some type of mechanical device that applies pressure to an artery, along with some other type of oscillation (pressure) sensor for the tonometric pressure estimation. Such a device is described in U.S. Pat. No. 6,730,038. Once again, devices of this type have proven unreliable during actual usage.

Other available methods for providing a continuous non-invasive blood pressure determination have tried to use formulas derived from the Bramwell-Hill equation. These methods utilize formulas that rely upon measured arterial pulse wave velocity (PWV) and measured arterial blood volume to determine blood pressure. In each of these methods, the arterial pulse wave velocity (PWV) and the arterial area must be measured. The required PWV measurements are typically obtained by observing the pulse transit time (PTT) between two widely separated sites, such as the heart and the finger tip. The pulse arrival times at the measurement sites, such as the finger tip, are typically determined by pleythysmography or pulse oximetry. One known method for determining PWV is described in U.S. Pat. No. 5,857,975. In this patent, the time of the pressure pulse's origin at the heart is determined from an EKG signal and the arrival time of the pulse is measured at another location on the patient. Based on these measurements, the instantaneous blood pressure is determined. In most systems, initialization data is obtained from a cuff based blood pressure determination and is used along with the time required for the pulse wave to travel between two points to calibrate formulas developed for continuously estimating blood pressure. After the initial calibration, changes in the pulse transit time can be related to changes in the blood pressure. In such schemes, the measurement of the area of the blood flow passageways, the blood flow, and PWV along with the subsequent blood pressure estimate are determined by the use of an assortment of complex adjustment factors.

In any type of non-invasive continuous blood pressure monitoring system, various factors can affect the accuracy of the measurement. For example, changes in the physiological state of the patient can bring about changes in the arterial wall elasticity. In general, changes in the arterial wall elasticity will affect the measured PWV. If the elastic modulus of the arterial wall changes, the same pressure may then need to be associated with a different cross-sectional area and PWV. If the operating point obtained using a blood pressure cuff calibration, then any changes in the arterial elasticity would require re-calibration, and if no re-calibration were performed, errors in the pressure estimation can clearly occur.

Another possible criticism of prior measurement systems concerns the measurement of the arterial blood volume. Specifically, the measurement of the arterial area by using pleythysmography is confounded by the highly elastic nature of the veins in the patient. Since the measurement includes some portion of the venous blood volume, it is difficult to rely upon the measurement to produce a total arterial lumen area. Venous blood volume is strongly affected by the subject position, since the hydrostatic pressure in the patient's body can cause pooling of the blood in highly distensible veins.

Yet another criticism of prior methods of making non-invasive blood pressure measurements concerns the manner in which the PWV measurements are made. Typically, any PWV measurement that is made between widely separated sites is measuring the PWV of a collection of branches of the arterial tree further complicating the relationship between PWV and blood pressure.

U.S. patent application Ser. No. 10/749,181, commonly assigned with the present application and incorporated herein by reference, teaches a method that utilizes pulse wave velocity to create a continuous, non-invasive blood pressure measurement. The '181 application teaches a method of measuring the pulse wave velocity within a patient and a method of relating such pulse transit time to blood pressure. Although the '181 application teaches a method of accurately measuring the PWV, the relationship to blood pressure can be criticized using some of the same grounds set forth above.

Thus, there is a desire to provide a more accurate, continuous, non-invasive blood pressure measurement technique and method.

SUMMARY OF THE INVENTION

The present invention is related to an apparatus and method for continuously and non-invasively monitoring the blood pressure that utilizes a transmission-line model and transcutaneous ultrasound measurements along a blood vessel of a patient. The resultant blood pressure measurements are displayed, in real time, to provide a continuous, non-invasive blood pressure measurement.

The apparatus of the invention includes at least a pair of ultrasound patch probes positioned along the skin of a patient. The ultrasound patch probes are separated by a relatively small distance and are positioned above the same blood vessel. The ultrasound patch probes are used by the system and apparatus of the present invention to make measurements relative to the blood vessel on a real time basis. Specifically, the ultrasound patch probes are used to determine the radius of the blood vessel and the blood flow rate at least two distinct locations along the length of the blood vessel. The ultrasound area and flow measurements are specific to the particular artery being used, unlike pleythysmography.

The system of the present invention utilizes a time-domain model of a transmission line where the electrical parameters of capacitance, inductance and resistance of the transmission line model are used in analogy to blood flow characteristics. Specifically, the capacitance of the electric circuit is analogous to the compliance of the artery, the inductance of the electric circuit is analogous to the inertia of the blood and the resistance is analogous to the viscosity of blood flow. The input and output current sources in the electrical transmission line model is analogous to the blood flow rate, which are determined at both ends of the modeled arterial segment using ultrasound measurement techniques.

Based upon the determined values in the model, a transmission line simulator becomes a circuit representation of the artery, where the voltage across the capacitor of the transmission line model correlates to blood pressure. The system of the present invention uses Kalman filter techniques to provide the best estimates of the state variables, which include the voltage across the capacitor in the transmission line model, which is analogous to a blood pressure measurement.

The system and apparatus of the invention utilizes a blood pressure cuff to provide initial calibration measurements for the blood pressure analysis performed in real time. The initiation blood pressure information is used to develop an initial state vector that forms part of the Kalman equation estimates. The system monitors the Kalman filter results, as well as other system variables, and automatically recalibrates the system using measured parameters when the current results of the Kalman filtering or the system variables, as compared to the initiation values, exceed a pre-defined threshold value.

The continuous, non-invasive blood pressure monitoring technique utilizes the pair of ultrasound patch probes to make accurate, real time measurements of physical characteristics of the blood vessel through which the blood flow is used to make a blood pressure measurement. The ultrasound patch probes provide accurate data that is used to provide better estimates for the blood flow and size of the blood vessels through which the blood pressure is being determined. In this manner, the continuous, non-invasive blood pressure monitoring method provides greater accuracy as compared to prior methods.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
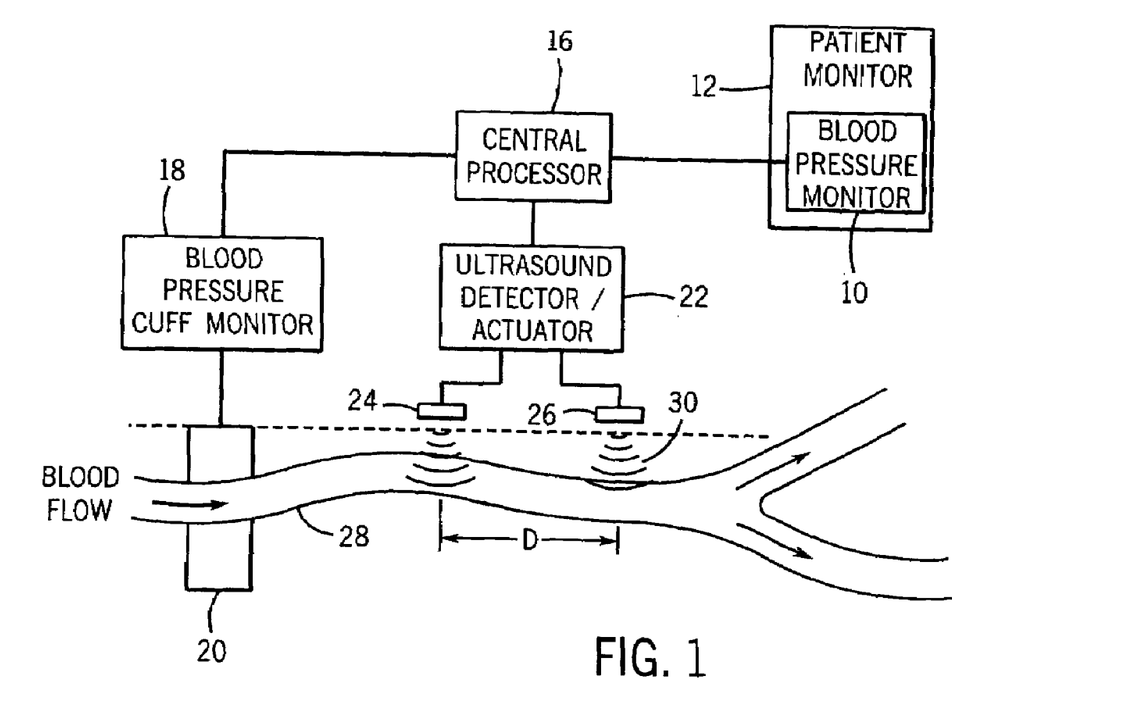
FIG. 1 is a illustration of the system of the present invention used to carry out the continuous, non-invasive blood pressure measurement technique.

Referring first to FIG. 1, a blood pressure monitor 10, which may be part of a larger patient monitor 12 is shown. The patient monitor 12 may provide medical personnel with information regarding different physiological functions of a patient 14. Specifically, the patient monitor 12 may include an electrocardiograph (ECG), a pulse oximeter, and the blood pressure monitor 10.

The patient monitor 12 is connected to a central processor 16 that is used to carry out the continuous, non-invasive blood pressure monitoring functions to be described in greater detail below. The central processor 16 is coupled to a blood pressure cuff monitor 18, which in turn controls and monitors the readings from a conventional blood pressure cuff 20. The blood pressure cuff 20 is shown positioned around the arm of a patient and can be operated in the conventional manner to obtain actual systolic and diastolic blood pressure readings from the patient 14.

The central processor 16 is also coupled to an ultrasound activation circuit 22, which in turn is coupled to a first ultrasound patch probe 24 and a second ultrasound patch probe 26. As illustrated in FIG. 1, the first ultrasound patch probe 24 and the second ultrasound patch probe 26 are spaced from each other by a distance D along the forearm of the patient. Although the first and second ultrasound patch probes 24, 26 are shown positioned along the forearm of the patient 14, it should be understood that the ultrasound patch probes 24, 26 could be positioned at various other locations along the patient.

As illustrated in FIG. 1, each of the ultrasound patch probes 24, 26 is positioned on the arm of the patient in such a manner as to enable non-invasive insonification of an artery. Each of the ultrasound patch probes 24 is positioned generally above the radial artery 28 of the patient. Likewise, the blood pressure cuff is positioned to sense blood pressure in the brachial artery of the patient.

The use of non-invasive ultrasound can provide volumetric flow, arterial lumen area and pulse wave velocity information. In addition, ultrasound measurements can be taken in such a way that all the data describes a single, uniform arterial segment (e.g., the brachial or common carotid arteries can be used). This means that the measured PWV is directly related to the mechanical properties of the segment of elastic tube (artery) for which the blood volume is being measured. In a patient monitoring application, the operator of the ultrasound device is eliminated through the use of software that automatically locates the artery in the ultrasound data, e.g., using known edge detection techniques. Autonomous operation of the ultrasound system allows it to report blood pressure and blood flow traces to the clinical users without those users having to interpret an ultrasound image or operate an ultrasound imaging device.

The use of ultrasound measurements in the continuous non-invasive blood pressure monitoring application is enabled by micromachined ultrasonic transducer patch probe technology, which allows ultrasound data to be taken using a thin, lightweight probe that adheres to the patient's skin. Recently, semiconductor processes have been used to manufacture ultrasonic transducers of a type known as micromachined ultrasonic transducers (MUTs), which may be of the capacitive (cMUT) or piezoelectric (pMUT) variety. cMUTs are tiny diaphragm-like devices with electrodes that convert the sound vibration of a received ultrasound signal into a modulated capacitance. For transmission, the capacitive charge is modulated to vibrate the diaphragm of the device and thereby transmit a sound wave.

One advantage of MUTs is that they can be made using semiconductor fabrication processes, such as microfabrication processes grouped under the heading "micromachining". As explained in U.S. Pat. No. 6,359,367:

> Micromachining is the formation of microscopic structures using a combination or set of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein. The systems resulting from such micromachining processes are typically referred to as "micromachined electromechanical systems" (MEMS).

The use of a MUT patch allows a clinician to attach the transducer to the patient's skin. The MUT patch is lightweight and flat. For the purpose of illustration, the ultrasound patch probes will be described that are made up of capacitive micromachined ultrasonic transducers (cMUTs). However, it should be understood that the patches could instead employ pMUTs.

An embodiment will now be described that incorporates a MUT patch. However, it should be understood that the present invention encompasses not only a device, but also methods for continuous non-invasive blood pressure monitoring, and that the basic method is not limited to devices that employ MUT technology. Instead, the basic method disclosed herein can also be performed by appropriately programmed ultrasound imaging systems having probes comprising conventional piezoceramic transducer elements.

Based on acoustic data from the cMUT ultrasound patch probes 24 and 26 and pressure data from the blood pressure cuff 20, the digital signal processor (DSP) 16 autonomously computes various parameters, including the patient's estimated blood pressure. In addition, the processor software forms and steers ultrasound beams over the volume of space in front of the cMUT ultrasound patch probes 24 and 26. Using both echo intensity and Doppler blood flow information, the software maps out the location of the vessel, its cross-sectional area, and the area increase at the time of passage of the systolic pressure wave. The pulse wave velocity can also be measured. This will yield useful information about the mechanical properties of the blood vessel wall.

The blood pressure cuff 20 is periodically inflated by the central processor 16 to provide the peak and steady state pressures at fixed points in time. More specifically, the processor 16 activates a pump to inflate the blood pressure cuff 20 with air. A blood pressure cuff monitor 18 detects the pressure in the cuff 20. The analog output of the cuff 20 is converted to a digital value by the cuff monitor 18, which digital pressure value is used by the processor 16. Initially, the processor 16 triggers cuff inflation in response to an activation command input by the system operator via an operator interface (not shown). Thereafter, the processor 16 triggers re-inflation of the cuff 20 for re-calibration whenever the estimated compliance value changes by more than some predetermined amount from its last calibration level. The results of the computations are displayed on a screen (not shown) of the patient monitor 10.

Although the pair of ultrasound patch probes 24, 26 and the blood pressure cuff 20 pneumatics in the disclosed embodiment are controlled and monitored by electronics coupled to the processor 16 by means of cables, obviously a wireless electrical coupling could be provided.

Figure 2:
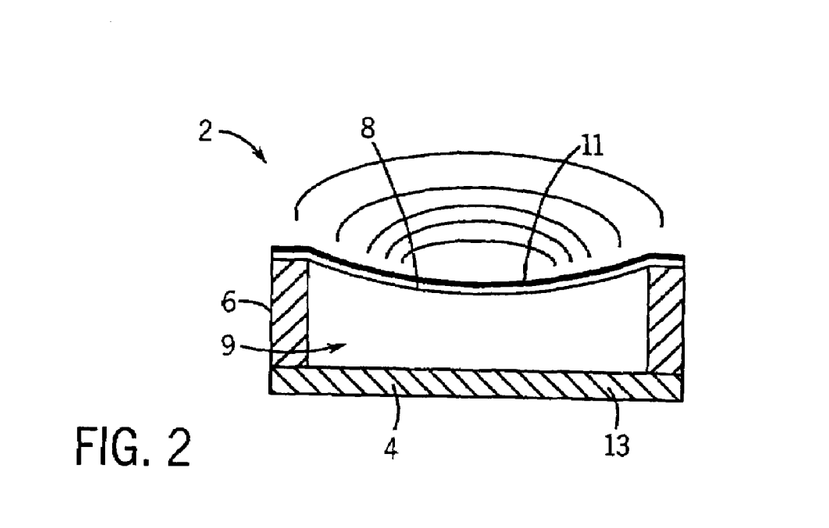
FIG. 2 is a drawing showing a cross-sectional view of a typical cMUT cell.

Referring to FIG. 2, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 9 between the membrane 8 and the substrate 4 may be air- or gas-filled or wholly or partially evacuated. A film or layer of conductive material, such as aluminum alloy or other suitable conductive material, forms an electrode 11 on the membrane 8, and another film or layer made of conductive material forms an electrode 13 on the substrate 4. Alternatively, the bottom electrode can be formed by appropriate doping of the semiconductive substrate 4.

The two electrodes 11 and 13, separated by the cavity 7, form a capacitance. When an impinging acoustic signal causes the membrane 8 to vibrate, the variation in the capacitance can be detected using associated electronics (not shown in FIG. 2), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

Figure 3:
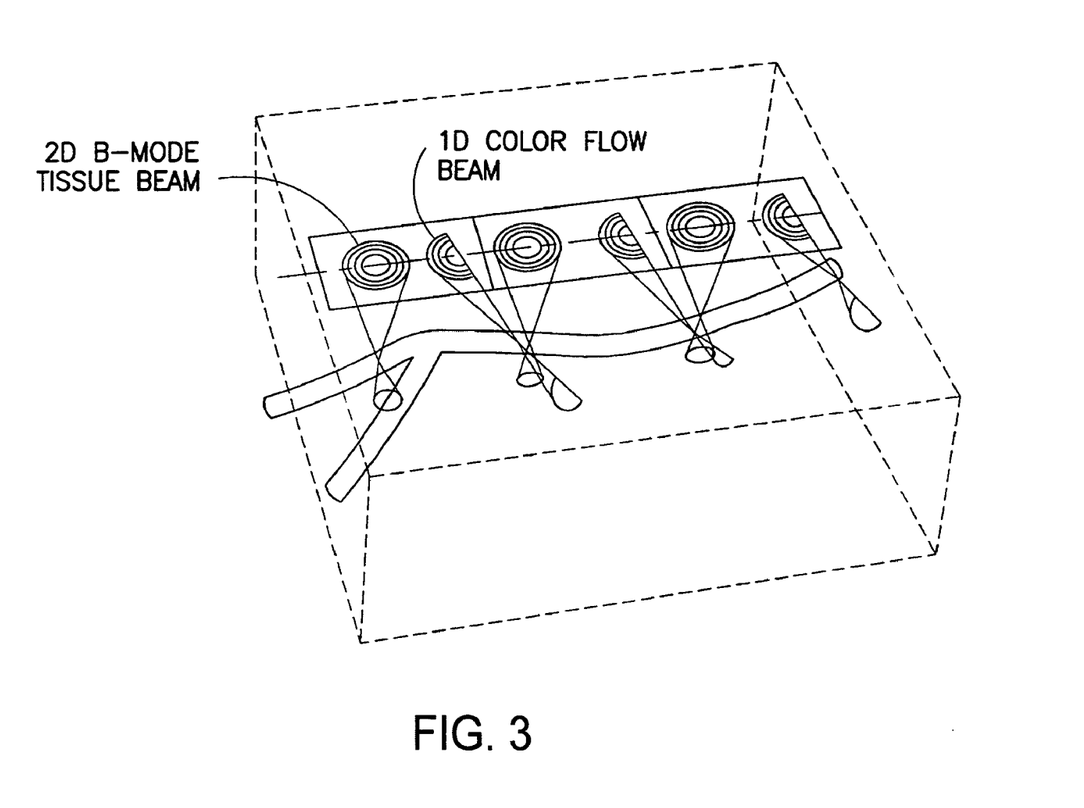
FIG. 3 is a drawing showing the CNIBP measurement concept in accordance with the disclosed embodiment of the invention.

For the CNIBP application, two types of data are acquired simultaneously using the cMUT patch, as shown in FIG. 3. The first data type is a sequence of B-mode images providing several short-axis views of the artery (in planes perpendicular to the direction of blood flow). Two or more short-axis views are taken along the length of the artery. The center of the artery can be found at each measurement location using edge detection techniques. The center of the artery can then be estimated for any location on the patch using interpolation. In addition to finding the artery center, the B-mode data is used to estimate the vessel diameter for the blood pressure calculation. More specifically, it is assumed that that the cross section of the lumen is a circle, so the estimated diameter can be used to calculate the lumen area A.

The second data type is a set of M-mode lines to be used for Doppler processing. The M-mode lines remain locked onto the center of the artery using information from the B-mode data. The multiple M-mode lines can be used with no Doppler steering angle for determining the velocity of the vessel wall or with a Doppler steering angle for determining blood velocities. The M-mode data, either wall or blood velocities, will be used for estimating the pulse wave velocity needed for the blood pressure calculation.

The two types of data are acquired by interleaving the acquisitions of the short-axis B-mode beams and the Doppler M-mode beams. A repeating scan sequence consists of a single B-mode beam at each location and all the M-mode beams. In the next pass through the sequence, the B-mode beams are translated across the patch while the M-mode beams remain in the same position. This is repeated until the desired width for the B-mode image is covered, generating a single frame of the B-mode data. Then the steps are repeated using any updated information about the vessel center. The result of the acquisition is M-mode data at a high repetition rate (~2 kHz), as required for Doppler processing, and the B-mode images at a slower rate (~100 Hz) determined by the required image size for vessel tracking.

The B-mode beams are translated across the cMUT patch by translating an annular array of activated sub-elements across the patch. A uniform translation of the beamforming coefficients produces a new beam at a different location. Repeated frequently, this generates a rectilinear two-dimensional image.

An additional bilinear term in the beamforming coefficients produces a beam directed away from the normal. Such beams are transmitted in the M mode to acquire data for Doppler processing that computes the blood velocity based on the Doppler Effect.

M-mode beams that are transmitted generally normal to the artery are used to acquire data for Doppler processing of the arterial wall velocity during deflection of the wall as the pulse wave travels down the artery. The maximum deflection occurs when the wall velocity is zero.

Referring back to FIG. 1, each of the first and second ultrasound patch probes 24, 26 can be actuated by the activation circuit 22 to emit an ultrasound pulse 30. The ultrasound pulse 30 allows the ultrasound activation circuit 22 to make multiple measurements and determinations relative to a uniform stretch of an artery, such as the brachial artery 28 positioned between each of the ultrasound patch probes 24, 26. In an alternate method of the present invention, the patch probes 24, 26 can be spaced on a range of artery in which there would be several bifurcations. In the embodiment of the invention illustrated, the ultrasound patch probes 24, 26 are shown spaced over a length of the unbifurcated brachial artery. Specifically, the central processors 16 can determine the internal diameter of the artery 28 at the location beneath the first ultrasound patch probe 24 and at the location beneath the second ultrasound patch probe 26. In addition to determining the diameter of the artery 28, the central processor 16 can utilize the Doppler ultrasound flow measurement technique to determine the instantaneous flow of blood at a first location beneath the first ultrasound patch probe 24 and at a second location beneath the second ultrasound patch probe 26. Thus, the central processor 16, through the ultrasound activation circuit 22 and the pair of ultrasound patch probes 24, 26 can determine the arterial diameter and blood flow rate at two separate locations along the radial artery which are spaced by the distance D. These two measurements made through the use of the ultrasound patch probes 24, 26 provide important and accurate information to the central processor 16 that aids in the determination of a continuous, non-invasive blood pressure measurement as described in detail below.

The data collection scheme associated with the present invention requires that at least two ultrasound probes be deployed along the length of a short arterial segment. In the monitoring application, it is anticipated that these will be the ultrasound patch probes 24 and 26. Each of these probes must have a steerable beam and must be able to operate at an angle with respect to the skin normal so that it can collect Doppler blood flow measurements. Such a probe can also be steered to the normal angle and used to measure the area of the artery's lumen. Optionally, other probes may be deployed between the two end probes, all of them at known locations along the line of the arterial segment.

Figure 4:
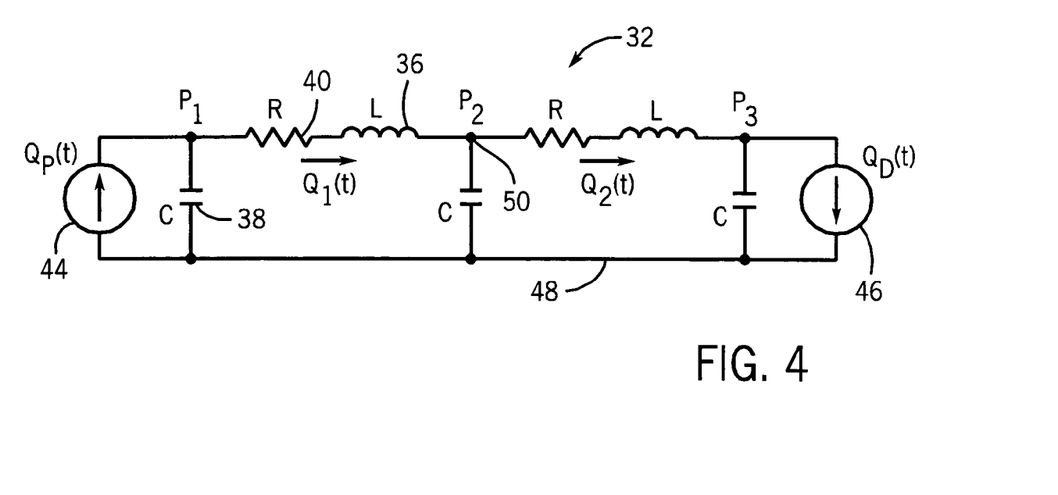
FIG. 4 is a schematic illustration of the transmission line model utilized to develop the blood pressure measurements of the present invention.

Referring now to FIG. 4, the blood pressure monitoring system and method of the present invention utilizes an algorithm in which a length of an unbifurcated artery is represented by a transmission line model 32. The transmission line model 32 shown in FIG. 4 is a well known model and technique used for determining the phase velocity of electrical waves propagating in a cable or transmission line. In accordance with the present invention, the transmission line model 32 can be analogized to the flow of blood in a distensible tube, and thus used to make blood pressure measurement. In the present approach, the transmission line is an analog for such a tube, with electric charge corresponding to fluid volume, current corresponding to volumetric flow and voltage corresponding to pressure. Thus, the specified flow measurements are like direct measurements of current in the analogous electric circuit.

In accordance with the present invention, the transmission line model 32 will be represented by a ladder network, each stage of which represents a short sub-segment of the arterial segment. The operation of this network can be represented by a set of simultaneous, first-order differential equations, which can be used to write a discrete-time state variable model for the system, given a sample rate. In the state variable model, half of the state variables will be pressures, the other half will be flows. This model can then be driven by ultrasound measurements and the pressure estimate will be given by one of the pressure state variables. Naturally, the model must have parameters that accurately represent the physical system in order to give meaningful results.

The general method of allowing a state variable model to evolve in time is reminiscent of the numerical solution of an initial value problem using Euler's method. The present apparatus approach differs from a typical initial value problem in that the equation to be solved is inhomogeneous, so if the system is stable, the particular solution associated with the driving function dominates the general solution. It is for this reason that the initial values of the state variables are ignored, except as described below in relation to the operating pressure.

The transmission line model 32 is represented in the signal processing method as a RLC lossless ladder network shown in FIG. 4. In the present application, the term "lossless" indicates that no mass (i.e. blood) is lost from the input to the output of the network, such as in a length of artery without any branching. The analogous quantity to the inductance L of the ladder network is the mass per unit length (per ladder network section) and the analogous quantity to the capacitance C is the elastic compliance of the tube. The resistors R represent energy loss due to the viscosity of blood. In the simplest version, the network is driven at both ends by current sources 44 and 46, representing the ultrasonic blood flow measurements.

Although the RLC ladder network in FIG. 4 is described as being a "lossless" network, it should be understood that if the method of the present invention is used on more complex artery structures, such as the radial artery, or a longer arterial segment, some of the blood mass is diverted in branching. In such an embodiment, a transverse resistance, in parallel with each capacitance, can be included in the ladder network. Although the present method does not use ultrasound measurements on the branching arteries, a relationship could be developed between changes in the dimensions and flow of the artery segments being measured and the branches that are not being measured. This relationship can be used to estimate the transverse resistance dynamically. Therefore, the presence of a transverse resistance can be handled within the scope of the described technique.

In the embodiment illustrated in FIG. 4, the transmission line model includes multiple RLC ladder network stages that each include an inductance 36, a capacitance 38 and a series resistance 40. The ladder network 34 includes n different stages.

In practice, the order of the transmission line model, which is related to the number of serial sections employed, is to be determined by the length of the arterial segment to be modeled, and the parameters represent values of an underlying distributed parameter, expressed per length of the individual section. For example, if the distance between the proximal and distal flow measurements is 5 cm (which is typical), then a 10-section transmission line model would have its compliance value given in units equivalent to "compliance per 5 mm section of tube". When the length of the individual section is short enough, then the compliance value in the model gives an approximate relationship between area and pressure. This corresponds to the definition of compliance used, for example, in the, Bramwell-Hill equation, discussed below.

The operation of the network of FIG. 4 is expressed in the following set of simultaneous ordinary differential equations:

$$Q_P - Q_1 = C\, dP_1/dt$$

$$P_1 - P_2 = RQ_1 + L\, dQ_1/dt$$

$$Q_1 - Q_2 = C\, dP_2/dt$$

$$P_2 - P_3 = RQ_2 + L\, dQ_2/dt$$

$$Q_2 - Q_D = C\, dP_3/dt \quad (1)$$

In the transmission line model, the state variables are the current through each of the inductors 36 as well as the voltage across each of the capacitors 38. In the present invention, the ground 48 of the transmission line model 32 is assumed to be zero such that the voltage across capacitor 38 represents the voltage at node 50. As previously indicated, the voltage in the transmission line model corresponds to pressure in the arterial transmission line model. (The ground value should actually be equal to the pressure in the venous system, but this is so low compared to the arterial pressures that it is negligible.) Thus, solving for the state variables and specifically the voltage across the capacitors 38, results in a value that is the instantaneous blood pressure estimate desired.

In matrix form, these equations are given by $$\begin{bmatrix} \dot{P}_1 \\ \dot{Q}_1 \\ \dot{P}_2 \\ \dot{Q}_2 \\ \dot{P}_3 \end{bmatrix} = \begin{bmatrix} 0 & -\frac{1}{C} & 0 & 0 & 0 \\ \frac{1}{L} & \frac{-R}{L} & \frac{-1}{L} & 0 & 0 \\ 0 & \frac{1}{C} & 0 & \frac{-1}{C} & 0 \\ 0 & 0 & \frac{1}{L} & \frac{-R}{L} & \frac{-1}{L} \\ 0 & 0 & 0 & \frac{1}{C} & 0 \end{bmatrix} \begin{bmatrix} P_1 \\ Q_1 \\ P_2 \\ Q_2 \\ P_3 \end{bmatrix} + \begin{bmatrix} \frac{1}{C} & 0 \\ 0 & 0 \\ 0 & 0 \\ 0 & 0 \\ 0 & \frac{-1}{C} \end{bmatrix} \begin{bmatrix} Q_P \\ Q_D \end{bmatrix} \quad (2)$$

where we use the notation $\dot{P}$ to denote the first derivative of P with respect to time.

Defining the vector of state variables $x = [P_1\, Q_1\, P_2\, Q_2\, P_3]^T$, we may write this as $$\dot{x} = Ax + B \begin{bmatrix} Q_P \\ Q_D \end{bmatrix} \quad (3)$$

where the matrices A and B are defined conventionally. Equation (3) gives a continuous-time expression for the transmission line model. The signal processing operation operates in discrete time, since the proposed measurements are intrinsically discrete time. In order to convert Equation (3) into an equivalent discrete-time model, a new state feedback matrix G is defined, which is the state transition matrix of the continuous system over the sample period. An input matrix F is defined that is equivalent to the effect of a constant input signal over the sample period:

$$\begin{aligned} x(k+1) &= e^{AT} x(k) + \left( \int_0^T e^{At}\, dt \right) B \begin{bmatrix} Q_P(k) \\ Q_D(k) \end{bmatrix} \\ &= Gx(k) + F \begin{bmatrix} Q_P(k) \\ Q_D(k) \end{bmatrix} \end{aligned} \quad (4)$$

This well-known-approach to discretization of a continuous time linear system represents a delay-free, zero-order hold assumption for the digitization of the driving signals. This is equivalent to representing the driving input signal by a piecewise constant approximation. Other digitization models can also be employed, such as a first-order hold, which represents the input signal as piecewise linear. Higher order hold models may be required at lower sample rates. Although the effects of quantization of the flow measurements are not included in this model, these effects can simply be considered as part of the additive observation noise.

The basic operation of the ladder network of the transmission line model is to integrate the two flow signals to get a time-varying volume estimate, and to scale that using the compliance (C) to obtain a pressure (P) estimate. The relationship between the cross-sectional area (A) of the lumen and the pressure is simply A=CP, and in a uniform tube, the volume (V) is simply Al, for a segment of length l. The series resistors 40, representing blood viscosity, are very important in implementing the low-pass frequency response characteristic that performs the integration.

In addition, the network implements a delay for the flow signals. Because of this delay, blood observed entering the system at a given time at one end will be canceled by blood leaving the system at a later time at the other end, with the interval determined by the implemented delay. This is true for the forward flow wave and also for the reflected, or retrograde, flow wave. When the delay does not match the actual delay in the system, the flow is cancelled either too soon or too late, with the result that the pressures are wrong. The phase velocity of the network depends on the product LC.

Most of the parameters of the ladder network 32 can be obtained from ultrasound measurements. The compliance is defined as $$C = \frac{dA}{dP} = \frac{2\pi r^3}{Ea} \quad (5)$$

where E is Young's modulus, a is the thickness of the arterial wall and r is the radius of the lumen. Although the product Ea cannot be measured directly using ultrasound, a quantity that is parameterized by it can be measured. Recently, a method for estimation of the arterial pulse wave velocity (PWV) that compensates for the effects of pulse reflections has been developed, as described in U.S. Patent application Ser. No. 10/749,181. This method can be used to determine the characteristic pulse wave velocity in a short arterial segment. We define the characteristic PWV as that velocity that would be observed in the absence of reflections. For this velocity, we have the Bramwell-Hill equation:

$$v_p = \sqrt{\frac{\pi r^2 dP}{\rho dA}} \quad (6)$$

where $\rho$ p is the density of blood. Substituting (5) into (6) and solving for C, we get $$C = \frac{\pi r^2}{\rho v_p^2} \quad (7)$$

so that the C parameter can be measured using PWV, arterial radius and the known density of blood. Note that these equations can also be solved for the Ea product. The blood mass/inertia parameter, L, is given by $$L = \frac{\rho}{\pi r^2} \quad (8)$$

this can be measured using only the arterial lumen radius. The serial resistance is given by:

$$R = \frac{8\eta}{\pi r^4} \quad (9)$$

where $\eta$ is the viscosity of blood. Because the viscosity cannot be directly measured by ultrasound, we can use a nominal constant for the viscosity. Alternatively, an adaptive process, described in detail below, can be used to adjust the viscosity until the model is correct.

Since there are no pressure sources in the transmission line model 32 of FIG. 4, and since the pressures enter into the equations only by way of first derivatives or of differences between two pressures, any constant could be added to the pressure variables without affecting the operation of the circuit, since the constant will be cancelled in every equation. Further, once a constant is added to the pressures in Equation 1, there is nothing to make it change, since there is no resistor to ground at any stage of the circuit. In practice, the mean pressure level will be set by a blood pressure cuff measurement. In a comparison of the measurements calculated using the present invention to simulated data, it has been found that the pressure state variables should be initialized to be slightly less than the mean pressure. Alternatively, several cycles of pressure observations can be run through the system, and the pressure state variables adjusted so that the mean pressure is that measured by the blood pressure cuff; this adjustment is done by the addition of the same quantity to all the state variables. If, at a later time, the compliance parameter changes, the mean pressure will change in response, since P=A/C, so that the same integrated flow will yield a different pressure. Such a change in mean pressure can also be used to trigger a recalibration using the cuff.

Figure 5A:
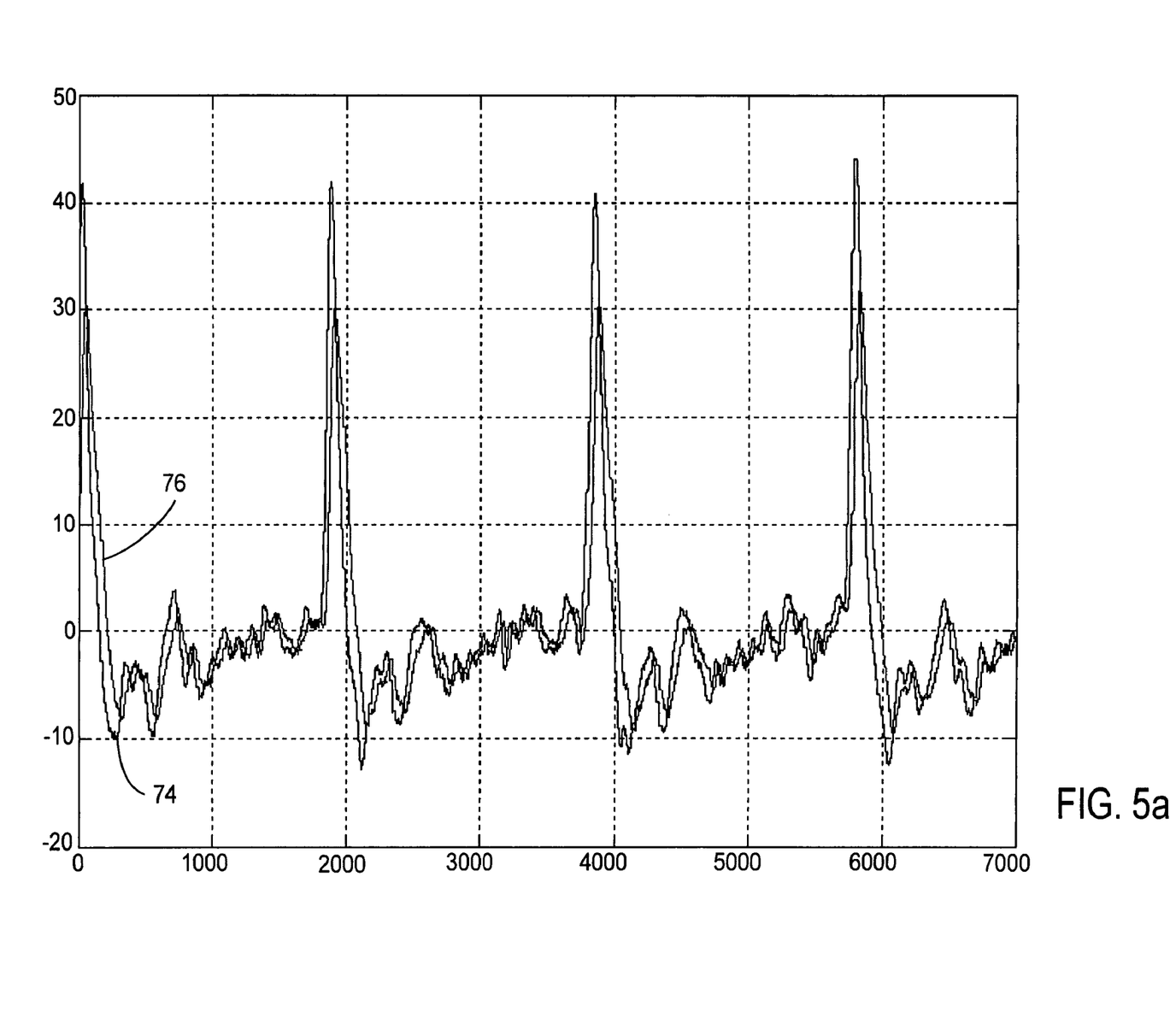
FIG. 5a is a graphic illustration of simulated proximal and distal blood flow.

As a means of showing the output waveforms that will be provided by this technique, a simulation was performed by taking a smoothed version of an impedance pleythysmography measurement from the femoral artery of a human subject, and taking its first difference to simulate a forward flow at the proximal measurement site. (Impedance pleythysmography measures the total blood volume at the measurement site.) The simulated proximal forward flow was delayed to get the forward flow at the distal site. A reflected flow wave was then added to both. The reflected wave as modeled as originating at a point 2 centimeters distal to the distal measurement site that reflected the wave with a reflection coefficient of 0.3. Since flow waves add algebraically, the reverse flow wave subtracts from the forward wave. Two cycles of the simulated total proximal flow 74 and distal flow 76 are depicted in FIG. 5a. Note that the distal flow appears more attenuated by the reflected flow because the reflection effect occurs sooner at the distal site.

Figure 5B:
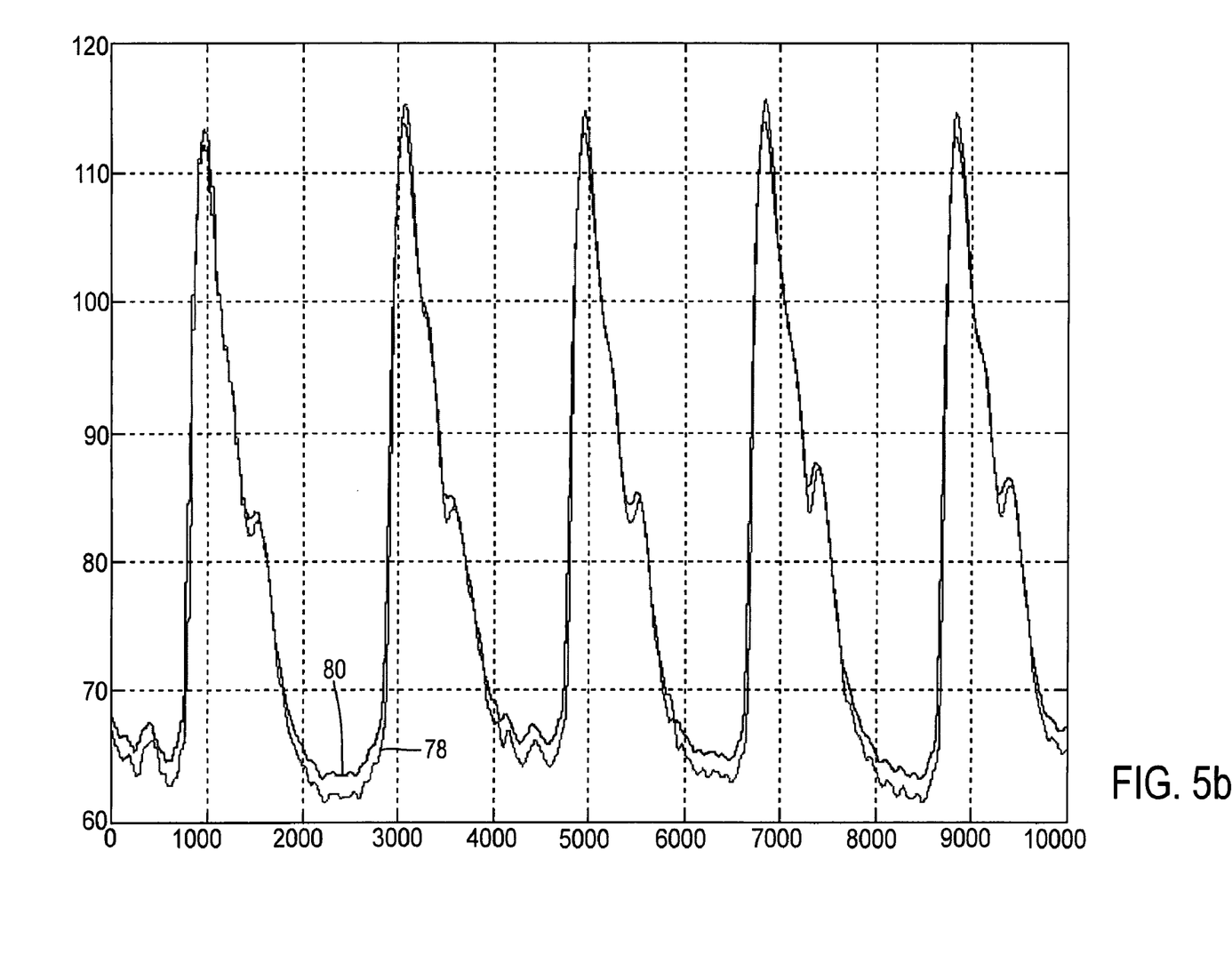
FIG. 5b is a graphic illustration of reconstructed pressure and actual pressure in accordance with the present invention.

FIG. 5b shows the result of inputting the flow waveforms on FIG. 5a in to the model above. The pressure variables of the model were initialized to a value of 70. The reconstructed pressure 78 is generally well-estimated, as compared to the actual pressure 80. The parameters of the model and the scale of the flow measurement were obtained by searching until a correct representation of the flow waveform occurred. Note that the simulation methodology did not enforce a consistent relationship between the delay, frequency response and scaling of the pressure variables. This example has been provided only to show the capability of the technique in producing a continuous non-invasive blood pressure waveform.

When additional measurements located between the two ultrasound patch probes 24 and 26 are available, it is not immediately clear how they should be used in the estimation scheme. What is clear is that they cannot be made sources, since that would have the effect of decoupling the sections of the model proximal and distal to the new source.

The answer to this dilemma is to turn the estimation procedure into a Kalman filter and to use the new observations as measurements, while retaining the original two measurements as system inputs. Using this approach, both flow and distension, or area, measurements can be incorporated, as available. Each measurement must correspond to a state variable that best represents its distance from the two ends of the model, defined by the two driving flow measurements.

The Kalman filter algorithm is composed of three main operations, which together recursively update the system state and its covariance matrix, which in turn determines the relative weight given to the observations as opposed to that given to the current state estimates. In the general form of the Kalman filter, the state update mechanism is taken to occur with additive noise. In accordance with the present invention, process noise is omitted from the model, or equivalently, the covariance matrix is set to zero.

In order to accommodate the new, interior observation sites, an observation matrix H is designed that specifies the observed state variables. In general, H has the same number of columns as the dimension of the state vector and the number of rows is equal to the number of additional observations. In each row, there is only one non-zero entry, which is unity if the measured state variable is a flow and C if the state variable is a pressure and the measurement is an area. The observation is then defined as $$z(k) = Hx(k) + v_k \tag{10}$$

where $v_k$ is an observation noise vector with covariance matrix $R = \mathrm{diag}(_n)$. The components of z(k) are either noisy flow measurements or noisy area measurements.

At the start of every iteration of the Kalman algorithm, it is assumed that an estimate of the current state vector denoted by $\hat{x}(k)$, is known, and its (time-varying) covariance matrix, denoted P(k), is also known. On the initial iteration, P(1) is set to a diagonal matrix with large entries, to represent the initial uncertainty in the state estimate. From the state and observation covariance matrices, the Kalman gain is computed, given by $$K(k) = P(k)H^T(HP(k)H^T + R)^{-1} \tag{11}$$

The innovations sequence is simply the difference between the observation and the observation that would be predicted by the current state vector. The Kalman gain matrix computed in Equation 11 is used to weight the innovations sequence to produce an updated estimate of the state vector at the $k^{th}$ sample time.

$$\tilde{x}(k) = \hat{x}(k) + K(k)(z(k) - H\hat{x}(k)) \tag{12}$$

Note that this equation replaces the current state vector by a weighted sum of itself and the observation.

The third and last step in the Kalman algorithm is to project the state vector and its covariance matrix to the next sample time:

$$\hat{x}(k+1) = G\tilde{x}(k) + F\begin{bmatrix} Q_P(k) \\ Q_D(k) \end{bmatrix} \tag{13a}$$

$$P(k+1) = G[(I - K(k)H)P(k)]G^T \tag{13b}$$

The effect of the Kalman filter is to replace the observed state variables at every step with a weighted average of their observed and predicted values. In the steady state, the weights depend to a large extent on the value of the noise variance on the main diagonal of R.

It is well-known that the actual compliance of arteries is not constant. The artery compliance is the slope of the transfer characteristic between pressure and the cross-sectional area of the vessel lumen. This characteristic is nonlinear because of the collagen fibers in the arterial wall, which are relaxed until a certain stage of the distension of the vessel, and then become taut, decreasing the elasticity. Thus, the compliance can be considered to be dependent on pressure. This nonlinear relationship can be represented by a piecewise linear relationship such that the compliance is different in a number of disjoint pressure ranges. This kind of pressure-dependent compliance can easily be incorporated into the time-domain approach above.

The pressure/area relationship has been modeled in the prior literature as an exponential. This transfer function was applied to a Windkessel model of the entire arterial system as seen from the aorta, and was found to have some advantages in terms of predicting the shape of observed pressure waveforms.

In the present model, the compliance enters into the definition of G, F and H. In order to implement pressure-dependent compliance, a different set of matrices must be implemented for every distinct pressure interval over which the compliance is constant. Equations (11), (12) and (13) are then executed using that set of matrices that is associated with the estimated pressure at step (k-1).

There are several features of flow estimation using ultrasound that must be kept in mind when implementing the method of the present invention. Volumetric flow estimation proceeds in the same way as ultrasound color flow mapping over a limited sector. Color flow mapping is a standard feature of most diagnostic ultrasound devices that estimates blood velocity at a number of locations on the image plane by computing the mean frequency of the spectrum of the returned ultrasound signal. This mean frequency corresponds to a mean Doppler shift induced by the moving blood. This measurement process involves insonifying a volume from which a blood velocity is desired, and this occurs from three to sixteen times for every estimate. This is done along several ultrasound A-lines. Once a set of blood velocity estimates is available at a number of locations covering the vessel lumen, the estimates are all multiplied by the area to which they individually apply and the products are summed. This implements an approximate integration over the lumen and the result is a volumetric flow.

However, ultrasound flow mapping can produce blood velocity estimates that are highly biased down from the true blood velocity if the ultrasound return contains significant energy from stationary tissue reflections. For this reason, the data used to compute the mean frequency estimates (the Doppler shifts) is typically high-pass filtered. This means that very low flows, such as might be encountered during diastole in a peripheral artery, may be missed. Since the majority of the flow undoubtedly occurs when the blood velocity is high, this may not be a major problem, but still, some portion of the flow is bound to be neglected due to this effect.

Another effect that can change the performance of the blood pressure measurement is the dependence of the ultrasound velocity measurement on angle. The measured phase change is indicative of the projection of the blood velocity vector on the ultrasound line. If the various flow measurements are based on different Doppler angles, they can be incommensurate. The lossless circuit of FIG. 4 requires that positive current entering the system at the proximal source 44 be canceled by negative current entering the system at the distal source 46 after some delay. If the angles of the two ultrasound lines are different, this cancellation will not take place, and the blood pressure will not be correctly computed. Note that if the ultrasound probes 24, 26 are mechanically connected to each other by a rigid structure, identical insonification angles are easily obtained.

No matter how many ultrasound lines are used to produce the velocity estimates, a new estimate can be computed for every new line, even though it will be highly correlated with the last such estimate. This means that a new volumetric flow estimate can be obtained for every frame. That is, the frame rate and volumetric flow sample rate are the same. The frame rate should be maximized by using only the minimum number of ultrasound lines required to cover the artery.

In the above discussion of the parameters of the transmission line model, it was noted that not all of the important parameters were directly observable using ultrasound. In particular, the product of the modulus of elasticity and the wall thickness (Ea), and the blood viscosity, represent two degrees of freedom not directly observable. We noted that the (Ea) product can be computed from pulse wave velocity, as long as the characteristic velocity rather than the apparent velocity, can be obtained, and that a method described in U.S. patent application Ser. No. 10/749,181 is available to obtain such velocity.

Alternatively, a data-adaptive processing can be utilized to find the undetermined free parameters of the model. This method, however, requires that at least one additional measurement be made, over and above the two required flow measurements described previously.

Many adaptive filters operate by minimizing a prediction error energy. In general, a prediction error is the error between the response of the filter to a known input and the response of the real system to that input. This is a well-known principle in spectrum estimation and system identification. In accordance with the invention, this approach is employed to indicate the degree of agreement between the parameters of the transmission line model and the state of the physical system.

For this purpose we use the model of the observations defined in Equation (10) in connection with the Kalman filter approach. The prediction error power at the $k^{th}$ sample is given by the squared norm of the $k^{th}$ element of the innovations sequence, and the prediction error energy is proportional to the prediction error power summed over some fixed period of time:

$$E_P = T_s \sum_{k=k_0}^{k_1} |z(k) - H\hat{x}(k)|^2 \quad (14)$$

where $T_S$ is the sample period.

The adaptive filter works by applying multiple sets of parameters to the data in parallel over a fixed period of time, and computing $E_P$ for each. The set of parameters producing the lowest prediction error energy is taken to be the correct set of parameters. The number of such parallel computations will obviously be limited by computational resources; however, even as few as three parallel computations will allow the adjustment of a single parameter. If one parameter set is chosen to be above the nominal parameter value, one chosen to be below it and another to be exactly at the nominal value, then after each observation period, the new nominal value can be that one of the three with the lowest $E_P$, and the process can be repeated. This allows the system to track a time-varying parameter with minimal computational resources.

The parameters that will typically be varied in this adaptation will be the (Ea) product and the blood viscosity, since the L parameter and the other components of the C and R parameters can be measured using ultrasound. Measurement of the characteristic pulse wave velocity of the artery can also be used to help estimate C. It is also possible to limit adaptation of these parameters to a region around the nominal value of η and the value of C predicted by the Bramwell-Hill equation.

Figure 6:
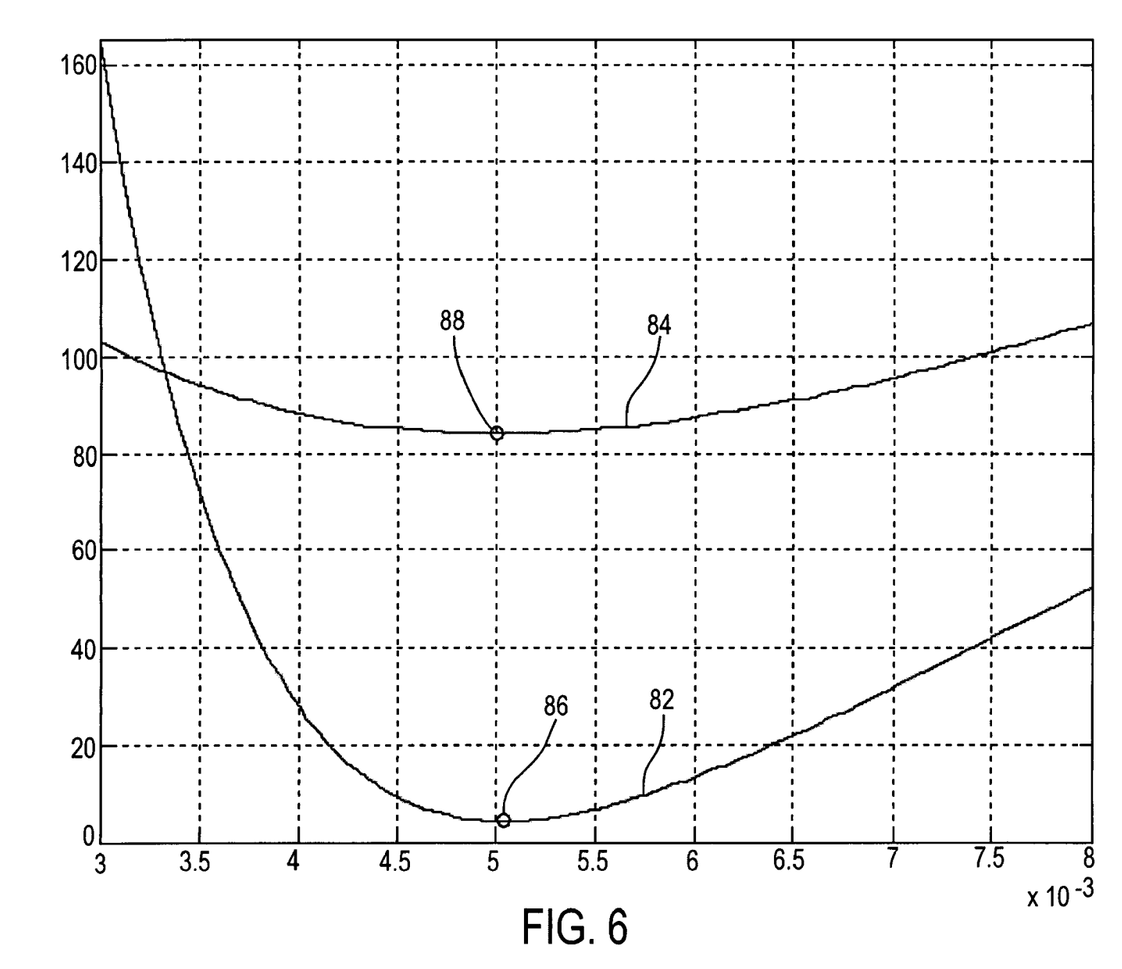
FIG. 6 is a graphic illustration of the error between estimated pressure and the known pressure with a prediction error.

As an example of the operation of the adaptive filter, the simulation example shown in FIGS. 5a and 5b above was repeated with a third, central, flow measurement, and with a range of compliance values around the optimum. The squared error between the known correct pressure and the predicted pressure, given knowledge of the correct mean pressure, was computed, along with the prediction error energy for predicting the third flow. The results are depicted in FIG. 6, in which the squared estimation error between the estimated pressure and the known pressure (line 82) is plotted against the prediction error (line 84). The two curves are in different units and they have been scaled and shifted so that they could be plotted on the same graph. The minimum value of each is marked by a circle 86 and 88. The plot shows that the prediction error curve 84 is smooth, and that it can be made to have the same minimum as the actual estimation error 84, provided the non-adapted parameters are correct.

Adaptation of the system parameters using prediction error is consistent with incorporation of the additional measurements using the Kalman filter. All that is required is the execution of the operations given by equations (11), (12) and (13b) in addition to the normal operation given above. There is a potential problem in this approach, however. To the extent that the observation used to generate prediction error updates the state variable to which it is compared, the sensitivity of the prediction error to model errors will be reduced. The degree to which the observations update the state variables is controlled by the noise variance specified in the R matrix; thus, adaptive Kalman filter operation will require that the adaptation occur during fixed periods, during which the noise variance is set to a high level. In periods when the adaptation is not taking place, the noise variance should be set back to a realistic level.

Figure 7:
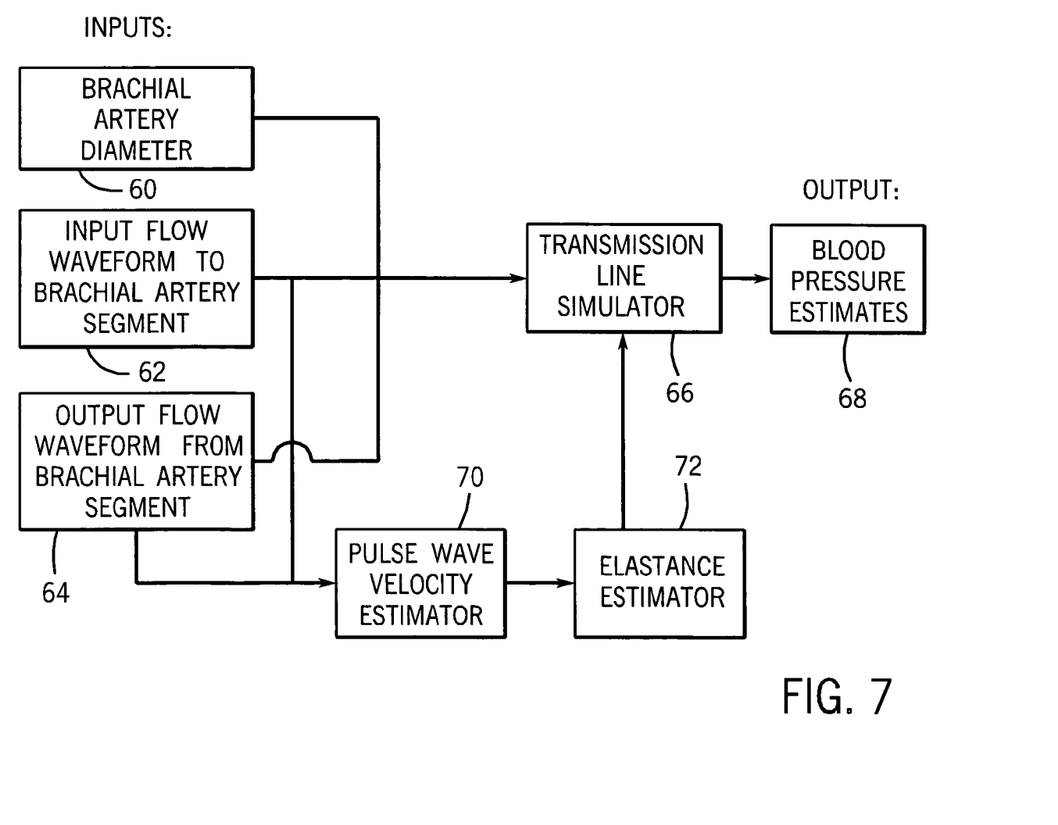
FIG. 7 is a high level data flow diagram illustrating the flow of data used to calculate the blood pressure estimates of the present invention.

Referring now to FIG. 7, there shown is the flow of data utilized for the continuous, non-invasive blood pressure measurement in accordance with the present invention. As shown on the left side of FIG. 7, the system receives a brachial artery diameter measurement in step 60. The artery diameter measurement is an ultrasound measurement taken from both of the ultrasound patch probes 24, 26 illustrated in FIG. 1. In addition to the diameter measurements, the input blood flow at ultrasound patch probe 24 is measured using ultrasound techniques. Likewise, the output blood flow is measured at block 64 by the ultrasound patch probe 26. The three ultrasound input measurements in blocks 60, 62 and 64 are all transferred to a transmission line simulator shown at block 66. The transmission line simulator 66 utilizes the input measurements, in connection with additional values to be described below, to carry out the calculation steps previously described. The transmission line simulator 66 includes the Kalman filtering as well as the state variable formulas to generate the blood pressure estimates, which are displayed in block 68.

The data flow also includes a pulse wave velocity estimator, which uses known measurement techniques, such as those taught in U.S. patent application Ser. No. 10/749,181 to calculate the pulse wave velocity. The pulse wave velocity estimator 70 also utilizes the input and output blood flow measurements from blocks 62, 64 to make an accurate pulse wave velocity estimate.

The data flow also includes an elastic estimator 72. The elastic estimator 72 utilizes the pulse wave velocity measurement from step 70 and an empirical formula to calculate the elasticity of the blood vessel through which the blood pressure is being determined. As illustrated in FIG. 7, the pulse wave velocity and elastic estimates are sent to the transmission line simulator 66 such that the transmission line simulator 66 can carry out the calculations to determine the blood pressure estimate.

In the present embodiment of the invention described above, the method and apparatus are described as presenting a continuous blood pressure measurement for a patient using ultrasound patch probes placed on the skin of the patient. Typically, this continuous measurement will be represented as a waveform that can be displayed. However, the method of the present invention is equally applicable for estimating the systolic and diastolic blood pressure for each beat of the patient's heart. The beat by beat estimate of the systolic and diastolic pressure would provide a continuous blood pressure measurement as the term is used herein.

What is claimed is:

1. A method for continuously and non-invasively monitoring blood pressure of a patient, the method comprising the steps of:
    positioning a first ultrasound sensor and a second ultrasound sensor aligned with a blood vessel of the patient, the first and second ultrasound sensors being operable to determine the diameter of the blood vessel and the flow rate of blood through the blood vessel;
    obtaining a first blood flow rate determined from the first ultrasound sensor, a second blood flow rate determined from the second ultrasound sensor, and a blood vessel radius;
    utilizing a transmission line model to represent the blood vessel, where the voltage at each node of the transmission line model corresponds to the blood pressure, the transmission line model including an input current source and an output current source positioned between an RLC ladder network, wherein the input current source is the first blood flow rate and the output current source is the second blood flow rate;
    developing a series of state variable equations based on the transmission line model; and
    inputting the obtained first blood flow rate, the second blood flow rate and the blood vessel radius into a Kalman filter;
    utilizing the Kalman filter to estimate the state variables of the transmission line model;
    using a transmission-line-based computation to estimate the blood pressure.

2. The method of claim 1 wherein the first and second ultrasound sensors are each aligned with the same blood vessel, the ultrasound sensors being spaced by a distance.

3. The method of claim 1 wherein the RLC ladder network includes an inductance (L), a capacitance (C), and a series resistance (R), wherein the capacitance is analogous to the compliance of the blood vessel, the inductance is analogous to the density of the blood divided by the cross-sectional area of the blood vessel and the series resistance is analogous to eight times the viscosity of blood divided by $\pi$ times the radius of the lumen of the blood vessel to the fourth power.

4. The method of claim 3 wherein the RLC ladder network further includes a transverse resistance corresponding to loss of blood mass due to branching from the blood vessel.

5. The method of claim 1 further comprising the steps of:
    determining the pulse wave velocity for the blood flowing through the blood vessel; and
    determining the capacitance (C) of the RLC circuit by $$c = \pi r^2 / \rho v_p^2$$

where r is the measured radius of the blood vessel, $\rho$ is the density of the blood and $v_p$ is the pulse wave velocity of the blood.

6. The method of claim 1 further comprising the steps of:
    comparing a current value of the state variables with an initialized value of the state variables; and
    re-initializing the measurement system when the current value of the state variables differs from the initialized value of the state variables by more than a pre-determined threshold value.

7. The method of claim 1 further comprising the steps of:
    continuously determining the radius of the artery of the patient;
    continuously determining the first blood flow rate and the second blood flow rate; and
    continuously updating the state variable equation with the blood vessel radius, first blood flow rate and second blood flow rate, such that the Kalman filter provides a continuous, real time blood pressure measurement.

8. The method of claim 1 wherein the state variable equations include at least one undetermined parameter, the method further comprising the steps of:
    providing multiple, separate estimates for the value of the undetermined parameter;
    calculating a prediction error for each of the estimates, wherein the prediction error is the difference between the response of the Kalman filter for the estimate and a measured blood pressure of the patient;
    selecting the estimate of the undetermined parameter that results in the smallest prediction error; and
    utilizing the selected estimate with the series of state variable equations and the Kalman filter to determine the continuous blood pressure.

9. The method of claim 1, further comprising:
    obtaining an initial blood pressure measurement with a blood pressure cuff; and
    using the initial blood pressure measurement as an initialization measurement for initializing the transmission line model for the transmission line-based computation.

10. The method of claim 9, further comprising attaching the blood pressure cuff to the patient at a location proximal to the patient's heart from the first ultrasound sensor.

11. The method of claim 9, further comprising determining the pulse wave velocity using the initial blood pressure measurement.

12. The method of claim 9 further comprising the step of utilizing the initialization measurement of the blood pressure to define an initial state vector used in the Kalman filter.

13. A method for continuously and non-invasively monitoring blood pressure of a patient, the method comprising the steps of:
    positioning a first non-invasive ultrasound sensor aligned with a blood vessel of the patient, the first ultrasound sensor being operable to determine a first diameter of the blood vessel and a first flow rate through the blood vessel;
    positioning a second ultrasound sensor spaced a distance from the first ultrasound sensor and aligned with the same blood vessel of the patient, the second ultrasound sensor being operable to determine a second diameter of the blood vessel and a second flow rate of blood through the blood vessel;
    creating a transmission line model to represent the blood vessel, wherein the transmission line model includes an RLC ladder network extending between an input current source and an output current source, wherein the input current source corresponds to the first blood flow rate determined by the first ultrasound sensor and the output current source corresponds to the second blood flow rate determined by the second ultrasound sensor; and utilizing a transmission-line-based computation to estimate the voltage at each node of the transmission line model, wherein the voltage corresponds to the blood pressure of the patient.

14. The method of claim 13 wherein the RLC ladder network includes an inductance (L), a capacitance (C), and a series resistance (R), wherein the capacitance is analogous to the compliance of the blood vessel, the inductance is analogous to the density of the blood divided by the cross-sectional area of the blood vessel and the series resistance is analogous to eight times the viscosity of blood divided by $\pi$ times the radius of the lumen of the blood vessel to the fourth power.

15. The method of claim 13 further comprising the step of initializing the measurement system by determining a measured blood pressure of the patient by utilizing a blood pressure cuff, the measured blood pressure being utilized to determine pulse wave velocity.

16. The method of claim 13 wherein the step of using the transmission-line based computation includes the steps of:
  developing a series of state variable equations based on the transmission line network;
  inputting the measured first blood flow rate, the measured second blood flow rate and a measured blood vessel radius into a Kalman filter; and
  utilizing the Kalman filter to estimate the state variables of the transmission line model, wherein the state variables include a capacitor voltage for each node in the transmission line model.

17. The method of claim 15 further comprising the steps of:
  determining the pulse wave velocity for the blood flowing through the blood vessel; and
  determining the capacitance (C) of the RLC circuit by $$c=\pi r^2/\rho v_p^2$$

where r is the measured radius of the blood vessel, $\rho$ is the density of the blood and $v_p$ is the pulse wave velocity of the blood.

18. The method of claim 16 further comprising the steps of:
  continuously determining the radius of the artery of the patient;
  continuously determining the first blood flow rate and the second blood flow rate; and
  continuously updating the state variable equation with the blood vessel radius, first blood flow rate and second blood flow rate, such that the Kalman filter provides a continuous, real time blood pressure measurement.

19. The method of claim 13 further comprising the step of:
  initializing the measurement system by determining an initialized value of the blood pressure of the patient by utilizing a blood pressure cuff, the initialized value of the blood pressure being used to solve the transmission line model.

* * * * *

UNITED STATES PATENT AND TRADEMARK OFFICE
CERTIFICATE OF CORRECTION

PATENT NO.        : 7,621,876 B2
APPLICATION NO. : 11/083259
DATED             : November 24, 2009
INVENTOR(S)       : Hoctor et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1287 days.

Signed and Sealed this

Twenty-sixth Day of October, 2010

David J. Kappos
*Director of the United States Patent and Trademark Office*